United States Patent [19]

Murabayashi et al.

[11] Patent Number: 5,414,122
[45] Date of Patent: May 9, 1995

[54] PROCESS FOR PRODUCING ALPHA-KETOAMIDE DERIVATIVE

[75] Inventors: Akira Murabayashi, Ibaraki; Hideyuki Takenaka, Nabari; Hiroyuki Kai, Yamatokoriyama, all of Japan

[73] Assignee: Shionogi & Co., Ltd., Osaka, Japan

[21] Appl. No.: 107,032

[22] Filed: Aug. 17, 1993

Related U.S. Application Data

[62] Division of Ser. No. 985,216, Dec. 3, 1992, Pat. No. 5,258,551.

[30] Foreign Application Priority Data

Dec. 18, 1991 [JP] Japan .................. 3-334858

[51] Int. Cl.$^6$ .......................... C07C 231/06
[52] U.S. Cl. ...................... 564/129; 544/316; 544/319; 544/336; 546/153; 546/171; 546/290; 546/329; 548/323.5; 548/326.5; 548/346.1; 548/366.1; 548/371.4; 548/341.1; 548/342.1; 548/373.1; 548/333.5; 548/375.1; 548/374.1; 548/325.1; 548/316.4; 548/376.1; 549/30; 549/429; 564/133; 564/142; 564/162; 564/167; 564/169
[58] Field of Search ............... 564/133, 142, 129, 169; 564/162, 167; 544/316, 319, 336; 546/153, 171, 290; 548/323.5, 326.5, 346.1, 366.1, 376.4, 341.1, 342.1, 333.5, 373.1, 375.1, 374.1, 325.1, 376.4, 376.1; 549/30, 429

[56] References Cited

U.S. PATENT DOCUMENTS

| | | | |
|---|---|---|---|
| 4,246,200 | 1/1981 | Wakselman et al. | 564/248 |
| 4,657,579 | 4/1987 | Milzner et al. | 71/92 |
| 4,929,273 | 5/1990 | Takematsu et al. | 564/175 |
| 5,258,551 | 11/1993 | Murabayashi et al. | 564/129 |

FOREIGN PATENT DOCUMENTS

| | | | |
|---|---|---|---|
| 2049162 | 3/1992 | Canada . | |
| 0178826 | 4/1986 | European Pat. Off. . | |
| 0477631 | 4/1992 | European Pat. Off. . | |
| 51329 | 12/1972 | Japan | 564/129 |
| 58-152846 | 9/1983 | Japan | 564/169 |
| 59-172448 | 9/1984 | Japan | 564/142 |
| 63-23852 | 2/1988 | Japan . | |
| WO86/00614 | 1/1986 | WIPO | 564/129 |

OTHER PUBLICATIONS

March, Advanced Organic Chemistry, Third Edition, 1985 p. 870.
Larock, Comprehensive Organic Transformation, 1989 pp. 963–964.

*Primary Examiner*—Shailendra Kumar
*Attorney, Agent, or Firm*—Wenderoth, Lind & Ponack

[57] ABSTRACT

There is disclosed an efficient process for producing α-ketoacetamide of the formula:

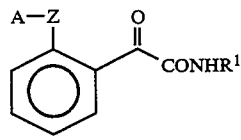

which is useful as an intermediate for the production of various alkoxyiminoacetamide compounds to be used for agricultural fungicides. In this process, a corresponding acid halide is condensed with isocyanide to produce the α-ketoacetamide.

9 Claims, No Drawings

PROCESS FOR PRODUCING ALPHA-KETOAMIDE DERIVATIVE

This is a divisional application of Ser. No. 07/985,216 filed Dec. 3, 1992, now U.S. Pat. No. 5,258,551.

FIELD OF THE INVENTION

The present invention relates to a process for producing α-ketoamide, which is an intermediate for production of alkoxyiminoacetamides useful as agricultural fungicides.

BACKGROUND OF THE INVENTION

Certain kinds of alkoxyimino compounds have been noted because they are known to have excellent fungicidal activities against microorganisms such as *Pyricularia oryzae, Rhizoctonia solani, Pseudoperonospora cubensis* and the like. Some of the compounds and their production have been known (JP-A 63-23852 and JP-A 63-30463).

The present inventors have already filed patent applications (JP-A 3-246268, JP-A 4-89464 and JP-A 4-182461, etc.) on the alkoxyiminoacetamide compound represented by the general formula (V):

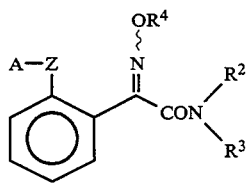
(V)

wherein A is a hydrogen atom, a halogen atom, alkyl, alkenyl, alkynyl, alkoxy, alkyl halide, alkenyl halide, alkynyl halide, cycloalkyl, cycloalkenyl, optionally substituted phenyl or optionally substituted heterocyclic group, Z is —CH₂—, —O—, —S—, —CH(OH)—, —CO—, —NR— (wherein R is a hydrogen atom or alkyl), —CH₂CH₂—, —CH=CH—, —C≡C—, —CH₂O—, —CH₂S—, —CH₂S(O)—, —OCH₂—, —SCH₂—, —S(O)CH₂— or epoxy, R² and R³ are the same or different and are a hydrogen atom, alkyl or cycloalkyl, R⁴ is alkyl or cycloalkyl, ~ indicates any configuration of the E isomer, Z isomer and the mixture thereof, and processes for producing it.

In these processes, the α-ketoamide of the general formula (III):

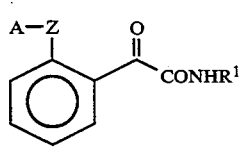
(III)

wherein each symbol is as defined above, is important as a common intermediate for the production of various alkoxyiminoacetamide compounds (V). For example, EP-A 398692 discloses a process for producing the α-ketoamide shown in the following scheme:

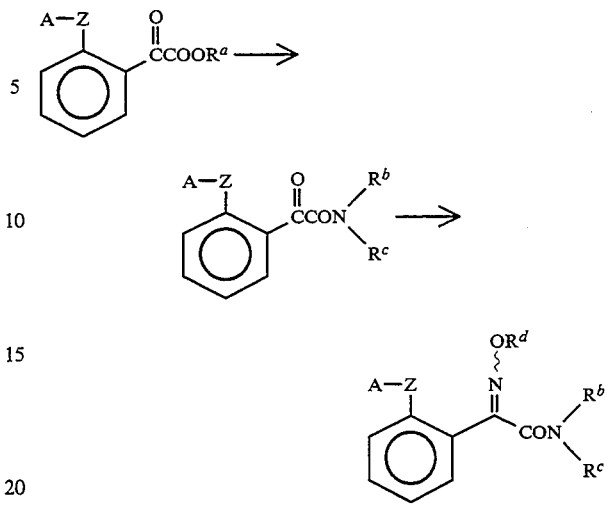

wherein Rᵃ is, for example, lower alkyl, and Rᵇ, Rᶜ and Rᵈ have the same meaning as R², R³ and R⁴, respectively.

However, this process employs as the starting material an α-ketocarboxylic acid ester which can be prepared with difficulty. Therefore, an improved production process thereof has been required by which not only the compound (III) but also its starting material can be produced economically and efficiently.

OBJECTS OF THE INVENTION

The main object of the present invention is to provide a process for producing an intermediate for the production of an alkoxyiminoacetamide compound which is useful as agricultural fungicides.

This object as well as other objects and advantages of the present invention will become apparent to those skilled in the art from the following description.

SUMMARY OF THE INVENTION

The present inventors have paid attention to usefulness of α-ketoamide of the general formula (III) as the common intermediate and have studied its production. As a result, it has been found that the ketoamide can efficiently be obtained by subjecting the corresponding acid halide to condensation with isocyanide followed by hydrolysis. Thus, the present invention has been completed.

That is, according to the present invention, there is provided a process for producing α-ketoamide of the general formula (III):

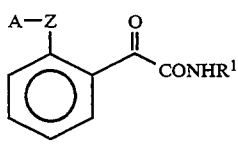
(III)

wherein A is a hydrogen atom, a halogen atom, alkyl, alkenyl, alkynyl, alkoxy, alkyl halide, alkenyl halide, alkynyl halide, cycloalkyl, cycloalkenyl, optionally substituted phenyl or optionally substituted heterocyclic group, Z is —CH₂—, —O—, —S—, —CH(OH)—, —CO—, —NR— (wherein R is a hydrogen atom or alkyl), —CH₂CH₂—, —CH=CH—, —C≡C—, —CH₂O—, —CH₂S—, —CH₂S(O)—, —OCH₂—, —SC- H₂—, —S(O)CH₂— or epoxy, and $R^1$ is alkyl or cycloalkyl, which comprises subjecting the acid halide of the general formula (I):

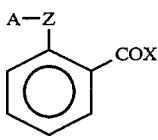  (I)

wherein X is a halogen atom and the other symbols are as defined above, to condensation with the isocyanide of the general formula (II):

$$R^1-NC \qquad (II)$$

wherein $R^1$ is as defined above, followed by hydrolysis. In the production process of the present invention, preferably, the acid halide of the general formula (I) is obtained by halogenating the carboxylic acid of the general formula (IV):

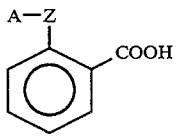  (IV)

wherein each symbol is as defined above.

DETAILED DESCRIPTION OF THE INVENTION

Examples of the alkyl represented by A, R, $R^1$, $R^2$, $R^3$ and $R^4$ in the above formula include alkyl having 1 to 6 carbon atoms, preferably 1 to 4 carbon atoms, for example, methyl, ethyl, propyl, isopropyl, butyl, isobutyl, t-butyl and the like.

Examples of the alkenyl represented by A include alkenyl having 1 to 6 carbon atoms, preferably 1 to 4 carbon atoms, for example, vinyl, allyl, crotyl and the like.

Examples of the alkynyl represented by A include alkynyl having 1 to 6 carbon atoms, preferably 1 to 4 carbon atoms, for example, propargyl, ethynyl, butynyl and the like.

Examples of the alkoxy represented by A include alkoxy having 1 to 6 carbon atoms, preferably 1 to 4 carbon atoms, for example, methoxy, ethoxy, propoxy, isopropoxy and the like.

Examples of the cycloalkyl represented by A, $R^1$, $R^2$, $R^3$ and $R^4$ include cycloalkyl having 3 to 7 carbon atoms, for example, cyclopropyl, cyclopentyl, cyclohexyl and the like.

Examples of the cycloalkenyl represented by A include cycloalkenyl having 3 to 7 carbon atoms, for example, cyclopentenyl, cyclohexenyl and the like.

The heterocycle in the heterocyclic group represented by A includes 5 or 6 membered heterocycles containing at least one hetero atom selected from the group consisting of nitrogen, oxygen and sulfur. The heterocycle may form a condensed ring with a benzene ring. Examples of the heterocycles include a pyridine ring, pyrimidine ring, pyrazine ring, thiazole ring, benzothiazole ring, benzofuran ring, benzothiophene ring, oxazole ring, benzoxazole ring, isoxazole ring, pyrazole ring, imidazole ring, quinoline ring and the like.

The phenyl represented by A and the above heterocyclic group is non-substituted or substituted with substituent(s) selected from alkyl, alkenyl, alkynyl, alkoxy, alkyl halide, alkynyl halide, cycloalkyl, cycloalkenyl, optionally substituted phenyl, optionally substituted heterocyclic group and a halogen atom. Examples of the alkyl, alkenyl, alkynyl, alkoxy, alkyl halide, alkynyl halide, cycloalkyl, cycloalkenyl, optionally substituted phenyl, optionally substituted heterocyclic group and halogen atom include the same alkyl, alkenyl, alkynyl, alkoxy, alkyl halide, alkynyl halide, cycloalkyl, cycloalkenyl, optionally substituted phenyl and optionally substituted heterocyclic group as those represented by A, respectively. When the phenyl or heterocyclic group represented by A is substituted, the number of the substituent is preferably 1 to 3 and the substituents are the same or different. The substituents may be at any possible position on the ring.

Examples of the halogen atom represented by A and X include fluorine, chlorine, bromine and iodine.

The alkyl halide, alkenyl halide and alkynyl halide represented by A means the alkyl, alkenyl and alkynyl described above which are substituted with at least one halogen atom described above, respectively.

In the production process of the present invention, the α-ketoamide of the formula (III) can be produced, for example, according to the reactions shown in Scheme 1:

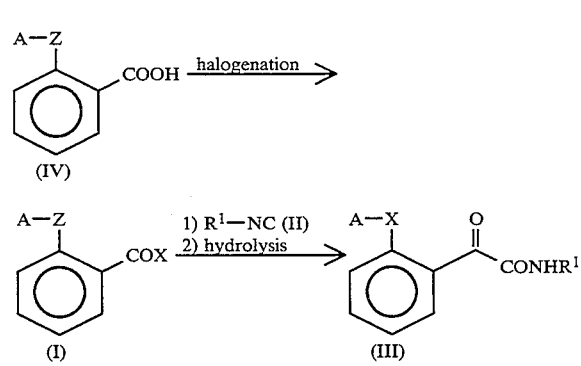

wherein each symbol is as defined above.

That is, the carboxylic acid (IV) is halogenated with a halogenating agent in an amount of 1 to 2 mol, preferably 1.1 to 1.2 mol per 1 mol of the carboxylc acid (IV) to obtain the corresponding acid halide (I). Examples of the halogenating agent include thionyl halide (e.g., thionyl chloride, thionyl bromide, etc.), phosphoryl halide (e.g., phosphoryl chloride, etc.), phosgene and the like. Examples of the solvent include hydrocarbons (e.g., benzene, toluene, etc.), halogenated hydrocarbons (e.g., chloroform, carbon tetrachloride, methylene chloride, 1,2-dichloroethane, etc.) and the like. The reaction temperature is 0° to 100° C., preferably 0° to 80° C. The reaction time is 0.5 to 3 hours, preferably 0.5 to 1 hours.

Next, the acid halide (I) thus obtained is subjected to condensation with the isocyanide (II). This reaction is carried out in the absence of a solvent or in an inert solvent such as hydrocarbons (e.g., benzene, toluene, etc.), halogenated hydrocarbons (e.g., dichloromethane, 1,2-dichloroethane, etc.), ethers (e.g., diethyl ether, tetrahydrofuran, etc.), ketones (e.g., acetone, etc.) and the like. The reaction temperature is 0° to 100° C., preferably 20° to 80° C. The reaction time is 1 to 10 hours. The alkyl isocyanide (II) is used in an amount of 1 to 2 mol, preferably 1.1 to 1.2 mol per 1 mol of the acid halide (I).

The isocyanide (II) can be prepared according to known methods, for example, the method described in Angew. Chem. Internat. Edit., vol. 4, No. 6, 472–484 (1965).

The isolation of the isocyanide (II) used in the condensation is not always required before use. The preparation of the isocyanide (II) according to, for example, the above known method and the condensation can be carried out in one-pot. For example, an alkylformamide (e.g., N-methylformamide, etc.) is reacted with phosgene, its dimer (e.g., trichloromethylchloroformate, etc.) or its trimer in the presence of a base (e.g., triethyl amine, etc.) in an inert solvent (e.g., toluene, etc.) to obtain isocyanide (II). The acid halide (I) is added to the reaction mixture containing the resulting isocyanide (II).

Then, hydrolysis is carried out in the absence or presence of a base or acid to obtain the desired α-ketoamide (III). Examples of the base include alkaline metal salts or alkaline earth metal salts (e.g., sodium hydroxide, sodium carbonate, potassium carbonate, sodium bicarbonate, potassium bicarbonate, calcium carbonate, etc.), amines (e.g., pyridine, triethyl amine, etc.) and the like. Examples of the acid include mineral acids (e.g., hydrochloric acid, sulfuric acid, nitric acid, etc.) and the like. The hydrolysis is carried out at 0° to 100° C. for 1 to 20 hours. If necessary, a hydrophilic solvent (e.g., acetone, tetrahydrofuran, etc.) is added for the hydrolysis.

The α-ketoamide (III) obtained according to Scheme 1 above is subjected to conventional separation and purification techniques to obtain the crude or purified product. The product can be used after conversion into, for example, an oxime for the production of the above alkoxyiminoacetamide (V) which is useful as agricultural fungicides, for example, (E)-2-(2-phenoxyphenyl)-2-methoxyimino-N-methylacetamide useful as fungicides for paddy fields, (E)-2-[2-(2,5-dimethylphenoxymethyl)phenyl]-2-methoxyimino-N-methylacetamide useful as fungicides for vegetables and fruit trees.

The present invention thus provides an efficient means for obtaining the α-ketoacetamide (III) which is highly useful as a common intermediate for the production of various alkoxyiminoacetamide compounds (V) available as agricultural fungicides.

The following examples and a reference example further illustrate the present invention in detail but are not to be construed to limit the scope thereof.

EXAMPLE 1

Preparation of N-methyl-2-(2-tolyl)-2-oxoacetamide

A mixture of 2-methylbenzoyl chloride (1.55 g) and methyl isocyanide (492 mg) was stirred at 60° C. for 6 hours. Then, the mixture was diluted with acetone (20 ml), and water (4 ml) and calcium carbonate (1.00 g) were added. The stirring of the resulting mixture was continued for 1 hour. The mixture was neutralized with dilute hydrochloric acid and extracted with methylene chloride. The organic layer was washed with saturated brine and dried over anhydrous magnesium sulfate. The solvent was evaporated under reduced pressure. The residue was subjected to column chromatography on silica gel and eluted with hexane-ethyl acetate (5:1) to obtain the title compound (1.71 g, Yield: 96.6%).

$^1$H-NMR (in CDCl$_3$, δ ppm): 2.49 (3H, s), 2.98 (3H, d, J=5.1 Hz), 7.06 (1H, brs), 7.26–7.31 (2H, m), 7.43 (1H, td, J=7.4,1.7 Hz), 7.92 (1H, dd, J=8.5,1.7 Hz).

EXAMPLE 2

Preparation of N-methyl-2-(2-tolyl)-2-oxoacetamide

Methyl isocyanide (0.84 ml) was added to 2-methylbenzoyl chloride (1.55 g). The mixture was stirred at 60° C. for 16 hours. Then, 5N hydrochloric acid (1.5 ml) and acetone (2 ml) were added, and the mixture was stirred at room temperature for 1.5 hours for hydrolysis. Then, water was added. The mixture was extracted with methylene chloride, washed with water and dried. The solvent was evaporated under reduced pressure to obtain the title compound as an oil (1.68 g).

EXAMPLE 3

Preparation of N-methyl-2-(2-phenoxyphenyl)-2-oxoacetamide

A mixture of 2-phenoxybenzoyl chloride (1.09 g) and methyl isocyanide (383 mg) was stirred at 50° C. for 3 hours. Then, the mixture was diluted with acetone (10 ml), and water (2 ml) and calcium carbonate (500 mg) were added. The resulting mixture was stirred for 1 hour. The mixture was neutralized with dilute hydrochloric acid and extracted with methylene chloride. After drying the organic layer, the solvent was evaporated under reduced pressure. The residue was subjected to column chromatography on silica gel and eluted with hexane-ethyl acetate (6:1) to obtain the title compound as crystals (1.04 g, Yield: 87.1%), mp: 94°–95° C.

$^1$H-NMR (in CDCl$_3$, δ ppm): 2.87 (3H, d, J=5.1 Hz), 6.64 (1H, brs), 6.88 (1H, dd, J=7.6,0.7 Hz), 7.06–7.12 (2H, m), 7.14–7.20 (2H, m), 7.32–7.39 (2H, m), 7.46 (1H, ddd, J=7.8,7.4,1.8 Hz), 7.75 (1H, dd, J=7.8,1.5 Hz).

EXAMPLE 4

Preparation of N-methyl-2-(2-phenoxymethylphenyl)-2-oxoacetamide

Methyl isocyanide (125 mg) and 2-phonoxymethylbenzoyl chloride (433 mg) were dissolved in toluene (2 ml). The mixture was stirred at 70° C. for 6 hours. The mixture was diluted with acetone (10 ml), and water (2 ml) and calcium carbonate (202 mg) were added. The resulting mixture was stirred for 2 hours. The mixture was neutralized with dilute hydrochloric acid and extracted with ethyl acetate. After drying, the solvent was evaporated under reduced pressure. The residue was purified by column chromatography on silica gel (hexane-ethyl acetate=4:1) to obtain the title compound as crystals (325 mg, Yield: 70.4%), mp: 78° C.

$^1$H-NMR (in CDCl$_3$, δ ppm): 2.72 (3H, d, J=5.1 Hz), 5.29 (2H, s), 6.88–6.99 (3H, m), 7.24–7.30 (2H, m), 7.41 (1H, m), 7.51–7.57 (2H, m), 7.89 (1H, d, J=7.6 Hz).

REFERENCE EXAMPLE 1

Preparation of 2-(2,5-dimethylphenoxymethyl)benzoic Acid

An aqueous solution (200 ml) of phthalide (134 g) and sodium hydroxide (40 g) was heated. After stirring for 1 hour, the mixture was concentrated under reduced pressure for removal of water to obtain sodium 2-hydroxymethylbenzoate as colorless crystals. p-Cymene (480 ml) and 2,5-xylenol (122 g) were added to the crystals. Azeotropic dehydration was carried out with heating under reflux for 7 hours by using an azeotropic dehydration apparatus. After cooling, ice water was added. Concentrated hydrochloric acid was added dropwise to make the mixture acidic. The precipitates were separated by filtration and recrystallized from ethyl acetate to obtain the title compound (155 g, Yield: 60.5%), mp: 162°–163° C.

$^1$H-NMR (in CDCl$_3$, δ ppm): 5.51 (2H, s), 6.71 (1H, d, J=7.3 Hz), 7.06 (1H, d, J=7.3 Hz), 7.42 (1H, t, J=7.7 Hz), 7.63 (1H, td, J=7.7,1.5 Hz), 7.88 (1H, d, J=7.7 Hz), 8.15 (1H, dd, J=7.7,1.5 Hz), 2.31 (6H, s).

EXAMPLE 5

Preparation of N-methyl-2-[2-(2,5-dimethylphenoxymethyl)phenyl]-2-oxoacetamide 2-(2,5-dimethylphenoxymethyl)benzoate (25.6 g) was dissolved in benzene (100 ml). Thionyl chloride (23.8 g) was added. The mixture was stirred at 60° C. for 1.5 hours. The benzene was evaporated under reduced pressure. Without isolation, the resulting acid chloride was diluted with dichloroethane (50 ml). Methyl isocyanide (8.20 g) was added, and the mixture was stirred at 40° C. for 12 hours. The mixture was diluted with acetone (200 ml), and water (40 ml) and calcium carbonate (10.0 g) were added. The mixture was stirred for 1 hour, neutralized with dilute hydrochloric acid and extracted with ethyl acetate. After drying the organic layer, the solvent was distilled off. The solid obtained was recrystallized from warmed toluene to obtain the title compound as colorless crystals (24.3 g, Yield: 82.1%), mp: 129°–130° C.

$^1$H-NMR (in CDCl$_3$, δ ppm): 2.16 (3H, s), 2.31 (3H, s), 2.79 (3H, d, J=5.1 Hz), 5.29 (2H, s), 6.68–6.70 (2H, m), 7.01 (1H, d, J=7.8 Hz), 7.44 (1H, t, J=7.8 Hz), 7.58 (1H, td, J=7.8,1.4 Hz), 7.66 (1H, d, J=7.8 Hz), 7.98 (1H, d, J=7.8 Hz).

EXAMPLE 6

Preparation of N-methyl-2-(2-phenoxyphenyl)-2-oxoacetamide

N-Methylformamide (2.36 g, 40.0 mmol) and triethyl amine (8.08 g, 80.0 mmol) were dissolved in toluene (40 ml). Trichloromethylchloroformate (3.96 g, 20.0 mmol) was added dropwise slowly under ice-cooling while maintaining the inner temperature at 10° C. or lower. The mixture was stirred at the same temperature for 1 hour. A large amount of insoluble materials were precipitated. To the mixture was added 2-phenoxybenzoyl chloride which was prepared from 2-phenoxybenzoic acid (4.28 g, 20.0 mmol) and thionyl chloride (2.86 g, 24.0 mmol). The resulting mixture was stirred at bath temperature of 40° to 50° C. for 26 hours. 5N-Hydrochloric acid (12 ml) and acetone (20 ml) were added, and the mixture was stirred for 12 hours. Water was added to the mixture, which was then extracted with toluene and purified by column chromatography on silica gel to obtain the title compound (3.11 g, Yield: 61.0%).

What is claimed is:

1. A process for producing an α-ketoamide of the formula (III):

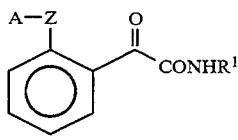 (III)

wherein A is a hydrogen atom, a halogen atom, alkyl, alkenyl, alkynyl, alkoxy, alkyl halide, alkenyl halide, alkynyl halide, cycloalkyl, cycloalkenyl, optionally substituted phenyl or optionally substituted heterocyclic group, Z is —CH$_2$—, —O—, —S—, —CH(OH)—, —CO—, —NR— (wherein R is a hydrogen atom or alkyl), —CH$_2$CH$_2$—, —CH=CH—, —C≡C—, —CH$_2$O—, —CH$_2$S—, —CH$_2$S(O)—, —OCH$_2$—, —SCH$_2$—, —S(O)CH$_2$— or epoxy, and R$^1$ is alkyl or cycloalkyl, which comprises halogenating a carboxylic acid of the formula (IV):

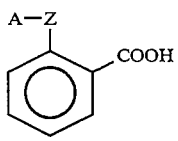 (IV)

wherein A and Z are as defined above, to produce an acid halide of the formula (I):

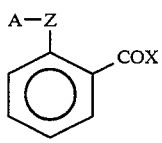 (I)

wherein X is a halogen atom and the other symbols are as defined above; and subjecting the acid halide to condensation with an isocyanide of the formula (II):

 (II)

R$^1$—NC wherein R$^1$ is as defined above, followed by hydrolysis.

2. A process according to claim 1, wherein the halogenating is conducted with a thionyl halide, phosphoryl halide or phosgene as a halogenating agent.

3. A process according to claim 1, wherein the halogenating is conducted with 1.1 to 1.2 mol of halogenating agent per 1 mol of the carboxylic acid of the formula (IV).

4. A process according to claim 1, wherein A-Z- is phenoxy and R$^1$ is methyl.

5. A process according to claim 1, wherein A-Z- is 2,5-dimethylphenoxymethyl and R$^1$ is methyl.

6. A process according to claim 1, wherein the condensation is carried out at 20° to 80° C.

7. A process according to claim 1, wherein the amount of the isocyanide of the formula (II) to be used is 1.1 to 1.2 mol per 1 mol of the acid halide of the formula (I).

8. A process according to claim 1, wherein the halogenation is carried out at 0° to 80° C.

9. A process according to claim 1, wherein the halogenation is carried out for 0.5 to 1 hour.

* * * * *